US007724369B2

(12) United States Patent
Yamaguchi et al.

(10) Patent No.: US 7,724,369 B2

(45) Date of Patent: May 25, 2010

(54) CORRELATOR

(75) Inventors: Tetsuji Yamaguchi, Shiga (JP); Shigeyuki Kawarabayashi, Kyoto (JP)

(73) Assignee: Horiba, Ltd. (JP)

( * ) Notice: Subject to any disclaimer, the term of this patent is extended or adjusted under 35 U.S.C. 154(b) by 38 days.

(21) Appl. No.: 12/245,902

(22) Filed: Oct. 6, 2008

(65) Prior Publication Data

US 2009/0091756 A1 Apr. 9, 2009

(30) Foreign Application Priority Data

Oct. 5, 2007 (JP) ............................ 2007-262161

(51) Int. Cl.
*G01N 15/02* (2006.01)

(52) U.S. Cl. .......................... 356/336; 702/29; 708/426

(58) Field of Classification Search ......... 356/335–343; 702/29, 179; 708/191, 426, 801, 425; 324/76.33, 324/76, 35, 76.36

See application file for complete search history.

(56) References Cited

U.S. PATENT DOCUMENTS 3,842,252 A * 10/1974 Jakeman et al. ............ 708/191
4,025,775 A * 5/1977 Beauvais et al. ............... 708/5
4,404,645 A * 9/1983 Elings et al. ................ 708/426
4,781,460 A * 11/1988 Bott .......................... 356/336
4,809,210 A * 2/1989 Pike et al. ................... 708/422
4,975,237 A * 12/1990 Watling ...................... 356/338
6,493,404 B1 * 12/2002 Iizuka et al. ................ 375/343
6,885,448 B2 * 4/2005 Tsutsui et al. ............... 356/336
2002/0180972 A1 * 12/2002 Ansari et al. ................ 356/336

FOREIGN PATENT DOCUMENTS

JP 2002-296118 A 10/2002
JP 2005249759 A * 9/2005

* cited by examiner

*Primary Examiner*—Hoa Q Pham
(74) *Attorney, Agent, or Firm*—Cantor Colburn LLP

(57) ABSTRACT

In order to improve an accuracy of an autocorrelation function, a correlator comprises a counter 61 for receiving a pulse signal at given time intervals (sampling times) and counting the number of pulses; a shift register 63 for receiving the number of pulses counted by the counter 61 and performing sequential time delay; an operation part 64 for performing a product-sum operation of an output from the counter 61 and that delayed by the shift register 63 for each channel; and a control part 65 for setting a delay time or a sampling time by the shift register 63 on a basis of a relationship of the Fibonacci sequence.

6 Claims, 5 Drawing Sheets

CORRELATOR

BACKGROUND OF THE INVENTION

1. Field of the Invention

The present invention relates to a sampling method in a photon correlation spectroscopy used for, for example, a particle size analyzer or the like.

2. Description of the Background Art

In measurements of particle size distribution based on the photon correlation spectroscopy (PCS), in addition to counting the number of photons (pulse signal) at a given sampling time depending on a scattered light intensity arising from particles to be measured, time is delayed with a shift register; a product-sum operation is performed to obtain an autocorrelation function; and a particle size (particle diameter) is calculated from a relaxation coefficient of the function.

Also, as the sampling method, a linear sampling method, exponential sampling method, multi-tau method, and the like are known.

However, these methods respectively have the following problems:

The autocorrelation function obtained by the photon correlation method is typically an exponential function for a particle with only monodispersive, and a shorter sampling time leads to a calculation result with higher accuracy; however, the linear sampling method is one in which the autocorrelation function of a pulse train is calculated at equal time intervals, and simple in circuit configuration and a control signal, but requires a large number of channels if a wide range of particle sizes is calculated with high accuracy. Also, even if the number of channels is sufficient for calculation, the sampling time should be adjusted depending on a particle size, resulting in the trade-off between the number of channels and an accuracy or time-consumption, and therefore the linear sampling method has a problem of practical difficulty in the use for the wide range of particle sizes.

Also, in the exponential sampling method, the sampling time is different for each channel so as to be able to cover the shortcoming of the above linear sampling method and be applied to the wide range of particle sizes, and as a stage proceeds, set to exponentially increase depending on a channel. However, in practice, the method has a problem that increasing the sampling time leads to a shortage of the number of data points on small particles, resulting in a reduction in accuracy, or the like.

Further, the multi-tau method is, as described in Patent document 1, one in which all channels are divided into blocks, and by linear sampling for channels in each of the blocks and exponential sampling between the blocks, the shortcomings of the above both methods are overcome and the advantages of the both are adopted, but has a problem that for a channel having a longer interval in a later stage block, a base line fluctuation, i.e., so-called bias noise, is increased, resulting in a reduction in accuracy of the autocorrelation function.

Patent document 1: Japanese Unexamined Patent Publication No. 2002-296118

SUMMARY OF THE INVENTION

Therefore, the present invention is made to solve the above-described problems at once, and an expected object thereof is primarily to improve an accuracy of the autocorrelation function.

That is, a correlator according to the present invention is characterized by including: a counter for receiving a pulse signal at given time intervals (sampling times) and counting the number of pulses; a sampling part for receiving the number of pulses counted by the counter; a delay part for receiving and sequentially delaying an output from the sampling part; an operation part for performing a product-sum operation of the output from the sampling part and the output delayed by the delay part for each channel; and a control part for setting a delay time or a sampling time $T_n$ for each of the channels to $$T_n = f_n \times T_o,$$

$$\text{where } f_n = a_{n-1} \times f_{n-1} + a_{n-2} \times f_{n-2} + a_{n-3} \times f_{n-3} + \ldots + a_1 \times f_1,\quad a_1 = \{0,1\}, \text{ and } i = n-1, n-2, \ldots, 1$$

(note that a series $f_n$ represents an integer geometric sequence of which a geometric ratio r asymptotically converges to $1 \leqq r < 2$, and $T_o$ represents a unit sampling time defined by a base clock).

This sort of configuration enables a correlator integrally handling the linear sampling method, the exponential sampling method, and the multi-tau sampling method to be designed. Also, as compared with the conventional exponential sampling method, a plurality of data points can be obtained. Further, if the number of channels is fixed, a time close to an optimum delay time or a sampling time can be expressed, and therefore an accuracy of the autocorrelation function can be improved and a circuit can be simplified. Still further, the sampling is performed at the delay times or sampling times that are integral multiples of a base clock, and therefore synchronized with the pulse signal, resulting in no missing or overlap count. Accordingly, the accuracy of the autocorrelation function can be improved. Besides, effects of being able to simplify the device and increasing the degree of freedom of measurement are also produced.

As a specific embodiment, it may be considered that the control part sets the delay time or the sampling time $T_n$ for each of the channels to $T_n = f_n \times T_o$ (where $f_n$ is, for example, a three-term recurrence formula). In particular, the embodiment includes that the delay time or the sampling time $T_n$ for each of the channels is set on a basis of a relationship of a Fibonacci sequence (converging to a ratio r=1.618), which is generally well-known, advanced in research, and expressed by the three-term recurrence formula as $f_n = f_{n-1} + f_{n-2}$, and the three-term recurrence formula represents that the next term one simply sums the preceding two terms.

Also, as in the multi-tau sampling, a plurality of channels may be grouped together, and a geometric ratio may be changed for each group. That is, it is also easy to divide all channels into a plurality of groups and configure a sampling time for each of the groups on a basis of a recurrence formula including a combination of different three terms. Preferably, as a method for setting the delay or sampling time, delay times or sampling times for first-half channels out of a plurality of (N) channels are set to meet a relationship of the linear sampling, and those for second-half channels are set on a basis of a relationship of a sequence formed from a multi-term recurrence formula.

If the $f_n$ cannot obtain a desired geometric ratio from the three-term recurrence formula, it may be considered that the control part sets the delay time or the sampling time $T_n$ for each of the channels to $T_n = f_n \times T_o$ (where $f_n$ is a four-term recurrence formula).

According to the present invention configured as above, even in a polydisperse system having a wide measurement range such as a range of six to seven orders of magnitude over which particle sizes and their distribution are dispersed, there is no missing or overlap pulse, and there is a guideline for optimizing the number of data points (number of channels) necessary to obtain the particle sizes (distribution), so that an accuracy of the autocorrelation function can be improved while enabling the measurement over a wide range, which is an advantage of a conventional exponential sampling.

DESCRIPTION OF THE PREFERRED EMBODIMENTS

First Embodiment

Figure 1:
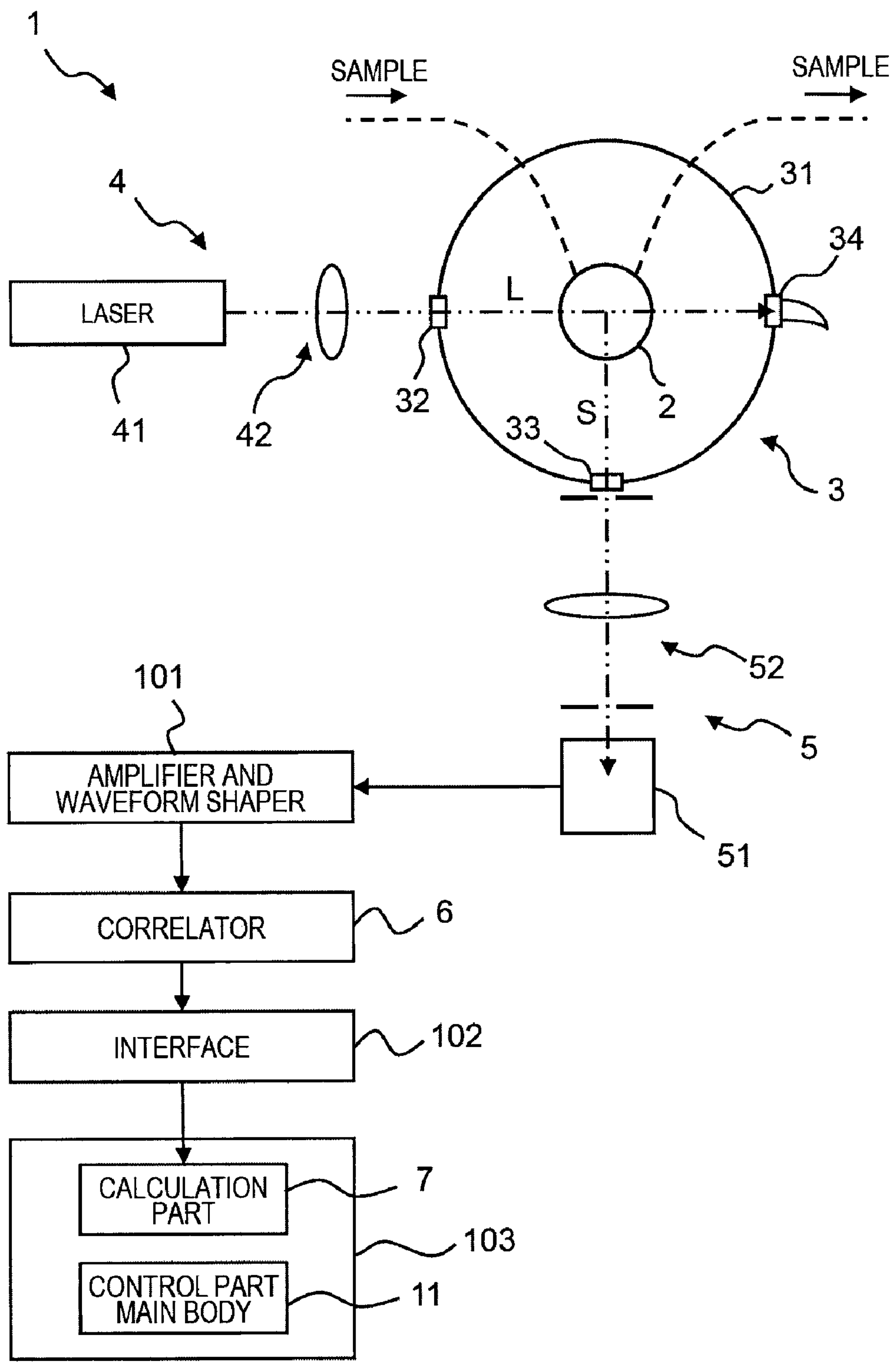
FIG. 1 is a schematic overall view illustrating a particle size analyzer according to one embodiment of the present invention.

A first embodiment of a particle size analyzer using a correlator of the present invention is described below referring to the drawings.

Figure 2:
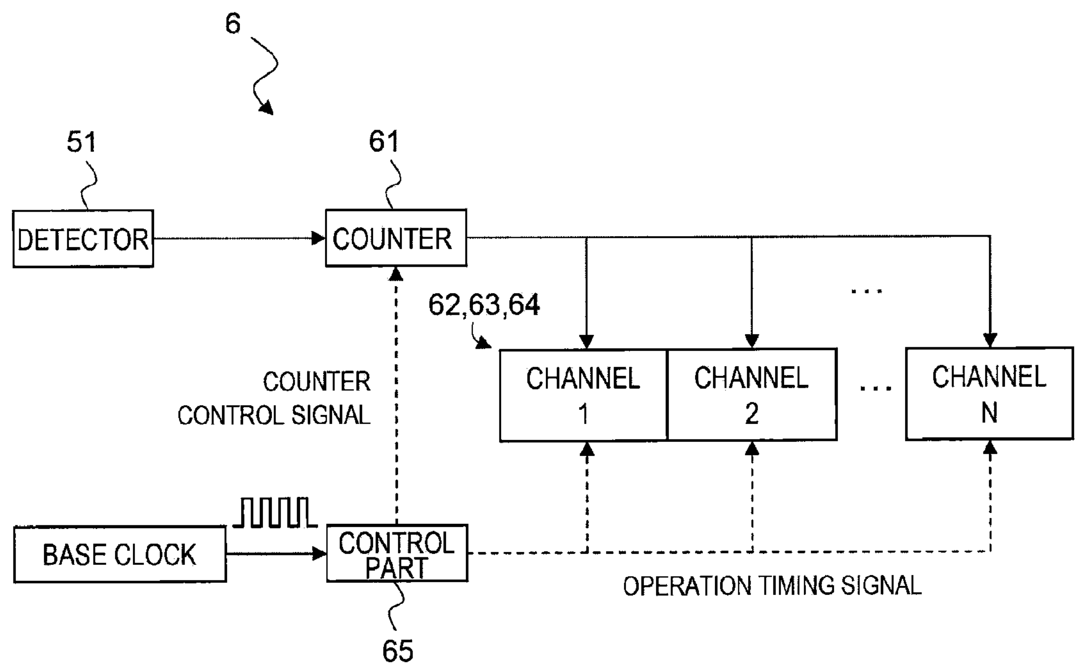
FIG. 2 is a hardware configuration diagram illustrating a hardware configuration in a same embodiment.
Figure 3:
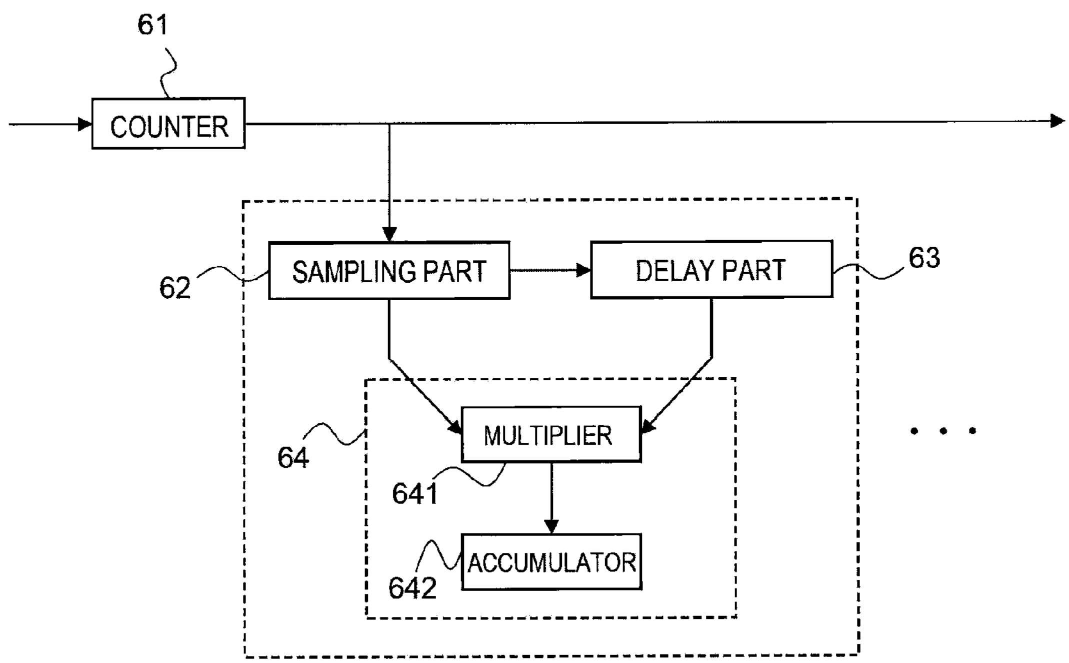
FIG. 3 is a configuration diagram of each channel in the same embodiment.
Figure 4:
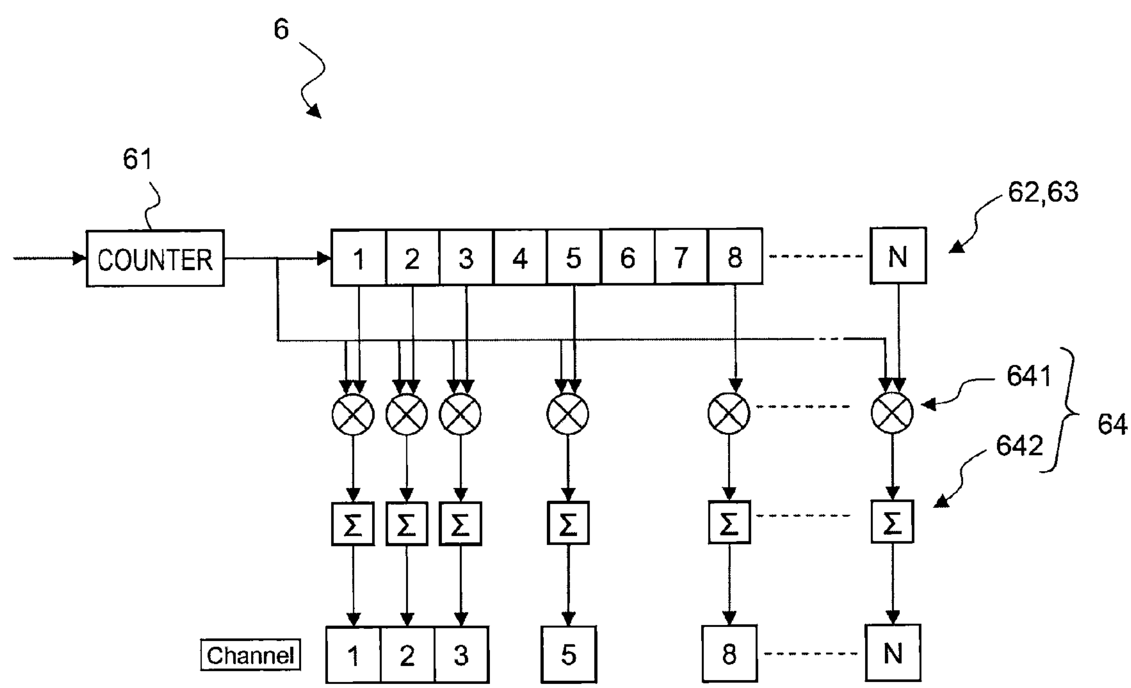
FIG. 4 is a hardware configuration diagram illustrating a hardware configuration in the same embodiment.

FIG. 1 is a schematic configuration diagram of a particle size analyzer 1 according to the present embodiment, and FIGS. 2 and 3 are hardware configuration diagrams illustrating a hardware configuration. Also, FIG. 4 is a timing chart illustrating opening/closing of a gate of a counter 61.

<Device Configuration>

The particle size analyzer 1 according to the present embodiment includes: as illustrated in FIG. 1, a transparent cell 2 for containing a sample configured to diffuse a particle group in a dispersion medium such as water; a bath 3 for soaking the cell 2 inside; a light irradiation part 4 for irradiating the sample with a laser beam L from outside the cell 2 through the bath 3; a light receiving part 5 for receiving scattered light S emitted from the particle group irradiated with the laser beam L and outputting a pulse signal depending on the number of photons of the scattered light S; a correlator 6 for receiving the pulse signal and generating autocorrelation data from time-series data on the number of pulses included in the pulse signal; and a calculation part 7 for calculating a particle size distribution of the particle group on a basis of the autocorrelation data obtained from the correlator 6.

The respective components 2 to 7 are described below.

The cell 2 is a hollow one formed of a transparent wall, and of a flow cell type configured such that the sample flows inside thereof in a constant direction at a given speed or less. The sample, which is fed from equipment for generating the particles, is introduced into the cell 2 from an inlet and discharged from an outlet.

The bath 3 is one in which transparent liquid having a refractive index close or equal to that of the cell 2 is filled inside a sealable hollow wall body 31, and contains the cell 2 in the middle inside thereof. The wall body 31 is formed of an opaque material, for example, a metal material, and provided with a laser beam window 32 and a scattered light window 33 both for light transmission in light paths of the laser beam L and scattered light S, respectively. In addition, reference numeral 34 provided in the wall body 31 on a side opposite to the laser beam window represents a light stopper for attenuating the laser beam L having been transmitted through the cell 2, to suppress reflection. Note that, in the present embodiment, the light paths of the laser beam L and the scattered light S are differentiated (the respective paths are orthogonalized in FIG. 1), but may be overlapped with each other.

The light irradiation part 4 includes: a light source, for example, a semiconductor laser 41; and a laser beam guiding mechanism 42 for focusing the laser beam L having been emitted from the semiconductor laser on a light irradiation area (e.g., center) inside the cell 2 through the laser beam window 32. The laser beam guiding mechanism 42 includes, for example, a condenser lens and the like.

The light receiving part 5 is one provided with: a photomultiplier tube (PMT) 51, which is a photodetector; and a scattered light guiding mechanism 52 for guiding the scattered light S having passed through the scattered light window 33 to the photomultiplier tube 51. The photomultiplier tube 51 outputs the pulse signal depending on the number of photons of the incident light as described above. The scattered light guiding mechanism 52 is one arranged with a lens between a pair of pinholes.

The correlator 6 is, as illustrated in FIGS. 2 to 4, provided with: a counter 61 for receiving the pulse signal and counting the number of pulses; a sampling part 62 for receiving the number of pulses counted by the counter 61; a delay part (shift register) 63 for receiving and sequentially delaying by a given time an output from the sampling part 62; an operation part 64 for performing a product-sum (multiplication and addition) operation of the output from the sampling part 62 and the output delayed by the delay part 63 for each channel; and a control part 65 for controlling timing of each of the respective components and input/output of data. In the present embodiment, the sampling part 62, delay part 63, and operation part 64 are provided for each channel, and the counter 61 is common to the respective channels. Also, a sampling time and a delay time for each of the channels are the same in the present embodiment.

The counter 61 is one for receiving the pulse signal and counting the number of pulses received with a gate being opened.

The sampling part 62 is one for receiving pulse number data indicating the number of pulses from the counter, and outputs the pulse number data to the delay part 63 and the operation part 64.

The pulse signal from the light receiving part 5 is, as illustrated in detail in FIGS. 2 and 3, input to the counter 61 through an amplifier and waveform shaper 101. The counter 61 is provided with the gate (not shown), and receives the pulse signal to count the number of pulses included in the pulse signal with the gate is opened.

Figure 5:
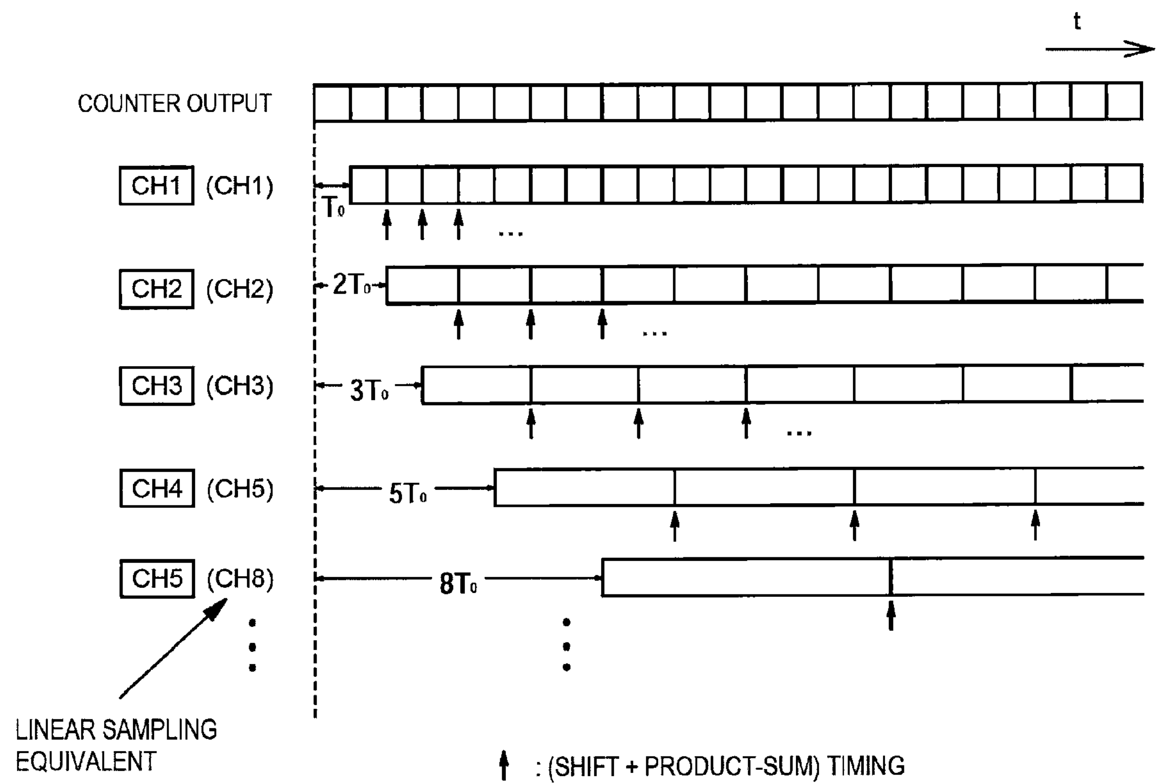
FIG. 5 is a timing chart illustrating opening/closing of a gate in the same embodiment.

Regarding the gate, as illustrated in FIG. 5, timing for opening the gate and an opening time period $T_o$ during which the gate is opened are controlled by a counter control signal transmitted from the control part 65.

The number of pulses counted by the counter 61 is sequentially transmitted to the sampling part 62 and the delay part 63. Also, during the transmission, the count number is reset. Note that, in the present embodiment, a minimum value of the gate opening time period is, for example, 10 ns.

The operation part 65 is, as particularly illustrated in FIG. 3, provided with a multiplier 641 and an accumulator 642. The operation part 64 multiplies the pulse number data, which is stored while being shifted to the respective channels in the delay part 64, by the latest one with the use of the multiplier 641, and accumulates pieces of the multiplied data with the use of the accumulator 642 to store the accumulated pieces of data in the accumulator 642 as the autocorrelation data.

Operation timings such as shift timing of the delay part 63, and calculation timings of the multiplier 641 and accumulator 642 are controlled by an operation timing signal from the control part 65.

The control part 65 is one for setting the delay time $T_n$ for each channel, and sets the delay time $T_n$ for a channel n to $T_n=f_n \times T_o$, where $f_n=a_{n-1}\times f_{n-1}+a_{n-2}\times f_{n-2}+a_{n-3}\times f_{n-3}+ \ldots a_1\times f_1$, $a_i=\{0, 1\}$, and $i=n-1, n-2, \ldots, 1$ (note that $f_n$ represents a normalized sampling time for the channel n, which is normalized with a unit sampling time $T_o$, and an integer geometric sequence of which a geometric ratio r asymptotically converges to $1 \leqq r<2$, n the number of channels, and $T_o$ the unit sampling time defined by a base clock).

Figure 6:
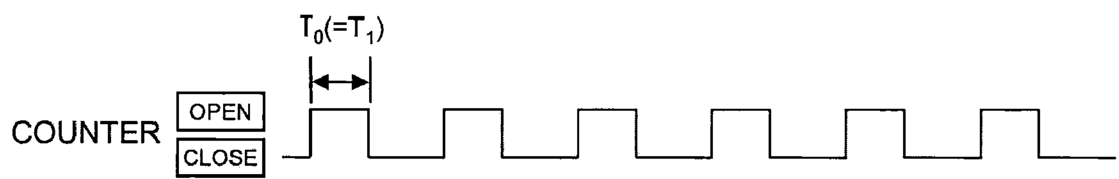
FIG. 6 is a diagram illustrating a delay time of each channel in the same embodiment.

Specifically, as illustrated in FIG. 6, given that a delay time $T_1$ for the first channel (CH1) is set to $T_o$ and a delay time $T_2$ for the second channel (CH2) set to $2T_o$, the control part 65 controls a delay time $T_3$ for the third channel (CH3) and that $T_5$ for the fourth channel (CH4) to be $3T_o$ and $5T_o$, respectively. That is, the control part 65 determines a delay time $T_n$ for the nth channel (CH(n)) according to a following expression. This indicates that the delay time is considered as a geometric sequence with a ratio of 1.618.

$$T_n=f_n \times T_o,$$

$$f_n=f_{n-1}+f_{n-2} (fn\text{: natural number}).$$

This sort of configuration requires the autocorrelation function up to 5 ms to measure particles having a particle size of, for example, 100 nm of which the relaxation time is 1 ms, and if the sampling is performed at $T_o$=50 ns, only 25 channels are required in the present embodiment, whereas the conventional linear sampling requires 100,000 channels.

That is, as illustrated in FIG. 4, in the delay part 63 having n channels, channels with numbers meeting a relationship of the Fibonacci sequence are connected with both of the multipliers 641 and the accumulators 642, whereas channels with numbers not meeting the relationship of the Fibonacci sequence (for example, CH4 or CH6 or the like) are not connected with any multiplier 641 or accumulator 642, resulting in a thinned structure.

A configuration from the counter 61 to the accumulator 642 can be a complete digital configuration using a discrete circuit, programmable logic circuit, and the like because the input signal corresponds to the number of photon pulses, i.e., a digital value, and is therefore highly reliable and accurate, low cost, and suitable for miniaturization.

A role of the calculation part 7 is played by an information processor 103 such as a computer installed with given software. The calculation part 7 obtains through an interface 102 the autocorrelation data that is stored in the accumulator 642 of the correlator 6 after the counting has been performed N times to complete the measurement, and calculates a particle size distribution of the sample according to a known given algorithm. A result of the calculation is, for example, displayed on a display.

Further, in order to optimize a measurement condition, the information processor 103 is provided with, by installing software, a control part main body 11 for: in addition to automatically or by an operator's input instruction outputting an instruction signal including a particle size expected to be measured, a flow rate of the sample flowing through the flow cell 2, concentration, color, and refractive index of the particles, and the like as parameters, controlling the light irradiation part 4 to control a laser power, and the control part 65 to control the gate opening time period and opening timing.

Effect of First Embodiment

According to the particle size analyzer 1 relating to the present embodiment configured as above, a larger number of data points can be obtained as compared with the conventional exponential sampling method. Also, if the number of channels is fixed, a time close to an optimum delay time can be expressed, and therefore an accuracy of the autocorrelation function and a measurement result can be improved and a circuit can be simplified. Further, the sampling is performed with the delay time having a natural number, and therefore there is no missing or overlap count of the pulse signal. This is the most important issue in the photon correlation method in which information on a diffusion coefficient due to the Brownian movement is obtained from a random signal, and a crucial requirement particularly in the case of a sparse measuring object. Also, effects of being able to simplify the device and increasing the degree of freedom of measurement are produced.

Second Embodiment

Next, a second embodiment of the particle size analyzer using the correlator of the present invention is described.

The particle size analyzer of the present embodiment is different from that of the first embodiment in terms of the delay time in the delay part 63 of the correlator. The control part 65 of the present embodiment is one for setting the delay time $T_n$ in the delay part 63 on a basis of the three-term recurrence formula other than that for the Fibonacci sequence.

That is, the control part 65 determines the delay time according to a following expression:

$$T_n = f_n \times T_o,$$

$$f_n = f_{n-1} + f_{n-3} (f_n\text{: natural number}).$$

Here, $$\begin{aligned} f_n &= f_{n-1} + f_{n-3} \\ &= f_{n-1} + (1/r) f_{n-2} \\ &= f_{n-1} + (1/r^2) f_{n-1} \\ &= (1 + 1/r^2) f_{n-1}. \end{aligned}$$

Accordingly, the sequence formed by the addition of the elements $f_{n-1}$ and $f_{n-3}$ of the geometric sequence with a ratio of r, i.e., $f_n=f_{n-1}+f_{n-3}$, can be considered as a geometric sequence with a ratio of $r_{13}$(=1.4656) if r takes a real root $r_{13}$(=1.4656) of $r^2(r-1)-1=0$. That is, a sequence {1, 1, 1, 2, 3, 4, 6, 9, 13, 19, 28, 41, 60, 88, 129, 189, 277, 406, 595, 872, 1278, . . . } can be obtained.

Also, if the required geometric ratio r is r=1.3, $f_n=f_{n-1}+f_{n-5}$ and $f_n=f_{n-2}+f_{n-3}$ are possible candidates for the three-term recurrence formula leading to r=1.325; however, because stability and convergence speed are affected by terms close to an initial value, a recurrence formula formed by terms closest possible to $f_n$ is desirable.

Third Embodiment

Next, a third embodiment of the particle size analyzer using the correlator of the present invention is described.

The particle size analyzer of the present embodiment is different from that of the first embodiment in terms of the delay time in the delay part 63 of the correlator. The control part 65 of the present embodiment is one for setting the delay time $T_n$ in the delay part 63 on a basis of the four-term recurrence formula.

That is, the control part 65 determines the delay time $T_n$ according to the following expression:

$$T_n = f_n \times T_o,$$

$$f_n = f_{n-1} + f_{n-5} + f_{n-6} (f_n\text{: natural number}).$$

This sort of recurrence formula can cause a geometric ratio to converge to 1.42, and a geometric ratio of $r=\sqrt{2}$ to be asymptotically provide. Specifically, the sequence of {1, 1, 1, 1, 1, 1, 3, 5, 7, 9, 11, 15, 23, 35, 51, 71, 97, 135, 193, 279, 401, 569, 801, 1129, . . . } can be obtained. This calculation result may be used as the sampling time without modification, or may be used to determine a sequence to be used for actual sampling. That is, the sequence may be determined as {1, 1, 1, 1, 1, 1, 3, 5, 7, 9, 10, 16, 24, 36, 50, 72, 100, 136, 192, 280, 400, 570, 800, 1130, . . . }.

<Other Variations>

Note that the present invention is not limited to the above-described embodiments. In a following description, members corresponding to those in the above-described embodiments are denoted by the same reference symbols.

For example, in the above-described embodiments, the correlator system of the present invention is applied to the dynamic scattering particle size analyzer, however, in addition to this, the correlator system can be applied to an analyzer for analyzing a sample or the like by using the photon correlation method, and also to an analyzer using the autocorrelation function.

Also, in the above-described embodiments, the delay time $T_1$ for the first channel is set to $T_o$, and that $T_2$ for the second channel is set to $2T_o$; however, in addition to this, the delay time $T_2$ for the second channel may be set to $3T_o$, and the delay time $T_n$ (n=1, 2, 3, . . . ) may be adapted to be $T_o$, $3T_o$, $4T_o$, $7T_o$, $11T_o$, $18T_o$, . . . (relationship of the Lucas sequence).

Further, in the above-described embodiments, all of the delay times meet the relationship of the Fibonacci sequence; however, in addition to this, a delay time $T_m$ for the first to m-th channels may be linearly changed, and that $T_n$ for the (m+1)-th to n-th channels may be set to meet the relationship of the Fibonacci sequence. This improves accuracy in baseline determination. Specifically, if the sampling time is linearly changed up to the fiftieth channel, and from the fifty-first channel, changed according to the relationship of the Fibonacci sequence, it can be {1, 2, 3, 4, 5, . . . , 49, 50, 99, 149, 248, 397, 645, 1024, . . . }.

In addition, the delay time $T_m$ for the first to m-th channels may be set to meet the relationship of the Fibonacci sequence, and that $T_n$ for the (m+1)-th to n-th channels may be set to meet the relationship of an exponential function.

Also, as in the multi-tau sampling, a plurality of channels may be grouped together, and a geometric ratio r may be changed for each group.

Besides, in the above-described embodiments, the sampling time appears at constant intervals, but may be exponentially increased.

Further, in the above-described embodiments, the control part 65 sets the delay time by the delay part 63 on a basis of the relationship of the Fibonacci sequence; however, in addition to this, the sampling time at which the gate of the counter 61 is opened may be set on the basis of the relationship of the Fibonacci sequence.

In the above-described embodiments, examples of the three-term and the four-term recurrence formulae are described; however, in addition to this, a five or more term recurrence formula may be employed.

Also, each of the recurrence formulae in the above-described embodiments preferably has an easy-to-solve combination of general solutions. For example, $f_n = f_{n-2} + f_{n-4}$ ($f_n$: natural number), or the like has a multiple root, and therefore r may be unstable depending on accuracy.

Further, in the above-described embodiments, there is only one counter 61; however, an embodiment using a plurality of counters 61 is allowed. Still further, the counter 61 may be provided for each channel. This makes it easy to fine adjust the delay time or sampling time.

Besides, the above-described embodiments and variations may be appropriately combined in whole or in part, and it should be appreciated that the present invention is not limited to the above-described embodiments, but may be variously changed without departing from the scope thereof.

What is claimed is:

1. A correlator comprising:

a counter for receiving a pulse signal at given time intervals and counting the number of pulses;

a sampling part for receiving the number of pulses counted by the counter;

a delay part for receiving and sequentially delaying an output from the sampling part;

an operation part for performing a product-sum operation of the output from the sampling part and the output delayed by the delay part for each channel; and a control part for setting a delay time or a sampling time $T_n$ for the channel n to $$T_n = f_n \times T_o,$$

$$\text{where } f_n = a_{n-1} \times f_{n-1} + a_{n-2} \times f_{n-2} + a_{n-3} \times f_{n-3} + \ldots + a_1 \times f_1, \quad a_i = \{0, 1\}, \text{ and } i = n-1, n-2, \ldots, 1$$

(note that a series $f_n$ represents an integer geometric sequence of which a geometric ratio r asymptotically converges to $1 \leqq r < 2$, and $T_o$ represents a unit sampling time defined by a base clock).

2. The correlator according to claim 1, wherein the control part sets the delay time or the sampling time $T_n$ for each of the channels to $$T_n = f_n \times T_o (\text{where } f_n \text{ is a three-term recurrence formula}).$$

3. The correlator according to claim 2, wherein the control part sets the delay time or the sampling time for each of the channels on a basis of a relationship of a Fibonacci sequence.

4. The correlator according to claim 3, wherein the control part sets delay times or sampling times for first-half channels to meet a relationship of linear sampling, and sets delay times or sampling times for second-half channels on a basis of the relationship of the Fibonacci sequence.

5. The correlator according to claim 2, wherein all channels are divided into a plurality of groups, and a sampling time for each of the groups is configured on a basis of a recurrence formula including a combination of different three terms.

6. The correlator according to claim 1, wherein the control part sets the delay time or the sampling time $T_n$ for each of the channels to $$T_n = f_n \times T_o \ (\text{where } f_n \text{ is a four-term recurrence formula}).$$

* * * * *